US012674788B2

(12) United States Patent
Muniraju et al.

(10) Patent No.: US 12,674,788 B2
(45) Date of Patent: Jul. 7, 2026

(54) GAS SENSOR DYNAMIC ENVIRONMENTAL COMPENSATION USING AUTO-CALIBRATION METHOD

(71) Applicant: Honeywell International Inc., Charlotte, NC (US)

(72) Inventors: Raghavendra Muniraju, Bangalore (IN); Nikhil Gupta, Delhi (IN)

(73) Assignee: HONEYWELL INTERNATIONAL INC., Charlotte, NC (US)

( * ) Notice: Subject to any disclaimer, the term of this patent is extended or adjusted under 35 U.S.C. 154(b) by 535 days.

(21) Appl. No.: 18/139,560

(22) Filed: Apr. 26, 2023

(65) Prior Publication Data

US 2024/0272130 A1 Aug. 15, 2024

Related U.S. Application Data

(60) Provisional application No. 63/445,880, filed on Feb. 15, 2023.

(51) Int. Cl.
*G01N 33/00* (2006.01)
*H03K 9/08* (2006.01)

(52) U.S. Cl.
CPC ........... *G01N 33/0008* (2013.01); *H03K 9/08* (2013.01)

(58) Field of Classification Search
None
See application file for complete search history.

(56) References Cited

U.S. PATENT DOCUMENTS 7,073,368 B2 7/2006 Wood et al.
7,640,783 B2 1/2010 Eickhoff 7,975,525 B2 7/2011 Bonne et al.
8,721,970 B2 5/2014 Willett et al.
11,141,549 B2 10/2021 Tolmie et al.
2006/0025897 A1* 2/2006 Shostak ............. G06K 19/0717
701/1
2020/0190971 A1 6/2020 Thiruvenkatanathan
2021/0099121 A1* 4/2021 Birkmayer .............. H02P 7/295
2022/0268722 A1 8/2022 Osswald et al.

FOREIGN PATENT DOCUMENTS

CN 109164216 A 1/2019
CN 112229958 A 1/2021
CN 112903758 B 9/2021
CN 113607329 A 11/2021

OTHER PUBLICATIONS

"Pellistor", Wikipedia, Retrieved from "https://en.wikipedia.org/w/index.php?title=Pellistor&oldid=1116560996", page was last edited on Oct. 17, 2022, at 05:35 (UTC).
Honeywell, "Unlock the Data Value in Your Field Instruments", https://process.honeywell.com/us/en/initiative/versatilis, downloaded Jan. 8, 2023.

* cited by examiner

*Primary Examiner* — Daniel S Larkin
(74) *Attorney, Agent, or Firm* — Ingrassia Fisher & Lorenz LLP

(57) ABSTRACT

A gas sensor system and a method of operating the gas sensor system can include a group of sensors and a microcontroller that can receive sensor measurements from the group of sensors. Feedback from the group of sensors can generate a sensor offset and a pulse width modulation (PWM) demodulator can be varied to reduce the sensor offset to null and provide sensor-to-sensor variations, which are independent of error in the sensor measurements.

15 Claims, 15 Drawing Sheets

106

| S. No. | PPM Change | Voltage Change with ppm (V) | Final Voltage from Sensor (V) | Resistance Value (Ohm) | PWM Input (Duty Cycle 0.0 - 0.0002 Seconds) | Output(mv) |
|---|---|---|---|---|---|---|
| 1 | 0 | 0 | | 47 | 0.00009192 | 56.2666 |
| 2 | 200 | 0.00016 | 1.50016 | 47.010028 | 0.00009193 | 56.1666 |
| 3 | 400 | 0.00032 | 1.50032 | 47.020058 | 0.00009194 | 56.1666 |
| 4 | 600 | 0.00048 | 1.50048 | 47.03009 | 0.00009195 | 56.1522 |
| 5 | 800 | 0.00064 | 1.50064 | 47.040124 | 0.00009196 | 56.1666 |
| 6 | 1000 | 0.0008 | 1.5008 | 47.05016 | 0.00009197 | 56.2666 |
| 7 | 1200 | 0.00096 | 1.50096 | 47.060199 | 0.00009198 | 56.1623 |
| 8 | 1500 | 0.0012 | 1.5012 | 47.07526 | 0.000091995 | 56.14536 |
| 9 | 1800 | 0.00144 | 1.50144 | 47.090327 | 0.00009201 | 56.17886 |
| 10 | 2000 | 0.0016 | 1.5016 | 47.100374 | 0.00009202 | 56.2167 |
| 11 | 3000 | 0.0024 | 1.5024 | 47.150641 | 0.00009207 | 56.3445 |
| 12 | 4000 | 0.0032 | 1.5032 | 47.200962 | 0.00009212 | 56.2666 |
| 13 | 5000 | 0.004 | 1.504 | 47.251337 | 0.00009217 | 56.2666 |
| 14 | 6000 | 0.0048 | 1.5048 | 47.301766 | 0.00009221 | 56.3464 |
| 15 | 7000 | 0.0056 | 1.5056 | 47.352248 | 0.00009226 | 56.6784 |
| 16 | 8000 | 0.0064 | 1.5064 | 47.402785 | 0.00009231 | 56.7666 |
| 17 | 9000 | 0.0072 | 1.5072 | 47.453376 | 0.00009235 | 56.8666 |
| 18 | 10000 | 0.008 | 1.508 | 47.504021 | 0.0000924 | 56.6678 |

108

PWM Input (Duty Cycle 0.0 - 0.0002 Seconds)

$y = 0.0000010x + 0.0000471$
$R^2 = 0.9995910$

PWM Duty Cycle

Sensor Resistance Value

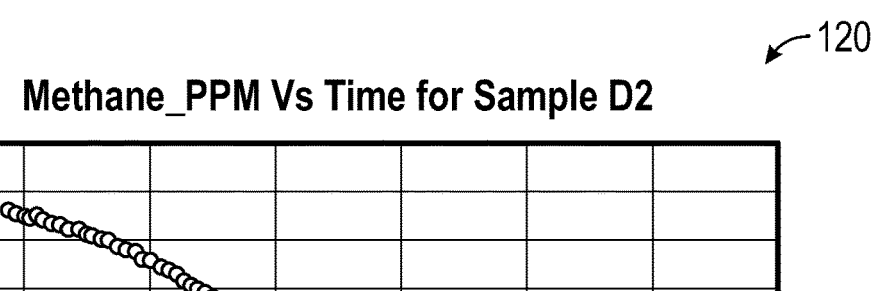
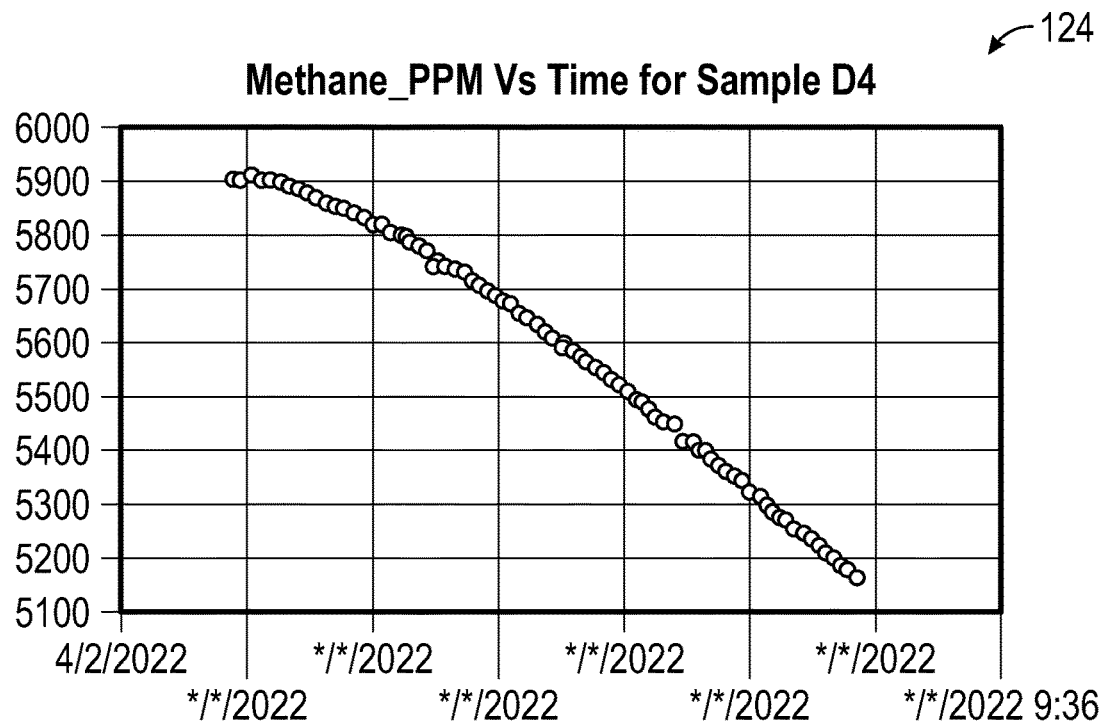
FIG. 8A
FIG. 8B

GAS SENSOR DYNAMIC ENVIRONMENTAL COMPENSATION USING AUTO-CALIBRATION METHOD

CROSS REFERENCE TO PROVISIONAL APPLICATION

This patent application claims priority under 35 U.S.C. § 119 to U.S. Provisional Patent Application Ser. No. 63/445,880 entitled "Gas Sensor Dynamic Environmental Compensation Using Auto-Calibration Method," which was filed on Feb. 15, 2023, and is incorporated herein by reference in its entirety.

TECHNICAL FIELD

Embodiments are generally related to gas sensors and emission monitoring. Embodiments further relate to gas sensors used in industrial plants and methods for auto-calibration of such gas sensors. Embodiments also relate to gas sensor systems and methods of operating such systems.

BACKGROUND

Modern industrial plants are faced with ongoing problems related to sustainability. There are several keys areas related to sustainability, which are faced by industry including problems related to global warming, plant efficiency, and plant worker safety.

Regarding global warming, methane emissions account for about 25% of the warming experienced today. Furthermore, natural gas operations leak 2.3% of the total gas extracted. In addition, methane has more than eighty times the climate-warming impact of $CO_2$ in the 20 years following its release from, for example, an industrial plant.

Plant efficiency problems stem from, for example, leaks that result in a loss of product—more than $30 billion each year. Other plant efficiency issues include reduced time spent on LDAR measurements and periodic EPA emission audits, along with carbon taxation. Plant work safety is another ongoing issue, which can be addressed with a continuous detection system.

The above problems may be addressed through gas sensing techniques. Conventional gas sensing technologies, however, such as metal oxide (MOX), catalytic combustion pellistor, non-dispersive infrared (NDIR), electrochemical, photoionization detector (PID), suffer from the effects of environmental conditions related to temperature, humidity, pressure, and long-term drift. For accurate measurement, these parameters may need to be compensated. Conventional compensation algorithms or circuitry used in gas sensing applications is complex and involves the implementation of these algorithms and circuitry during the manufacturing process, which makes such gas sensors expensive and, in some cases, impractical for real-world sensing applications.

For accurate and reliable measurement of gas leakage, the above effects must be compensated. The conventional compensation methods would need complex calibration algorithm and or a look-up table for every sensor in the production. The compensation algorithm I correction equation should reside in the sensor or in the cloud with appropriate device identification because of unique calibration coefficient. The gas sensor cost increases because of the special production process and binning. Commercially available smart sensors include compensation methods, which are unfortunately expensive, and may require passive raw sensors, such as MEMS mox, pellistor, etc., and may not meet the product functional requirements because of low sensitivity and accuracy issues.

BRIEF SUMMARY

The following summary is provided to facilitate an understanding of some of the features of the disclosed embodiments and is not intended to be a full description. A full appreciation of the various aspects of the embodiments disclosed herein can be gained by taking the specification, claims, drawings, and abstract as a whole.

It is, therefore, one aspect of the disclosed embodiments to provide for an improved gas sensor system and method of operating the gas sensor system.

It is another aspect of the disclosed embodiments to provide for auto calibration and dynamic compensation hardware and an associated method that can eliminate the need for special characterization and calibration processes.

The aforementioned aspects and other objectives can now be achieved as described herein. In an embodiment, a gas sensor system, can include a plurality of sensors, a microcontroller that receives sensor measurements from the plurality of sensors, and a pulse width modulation (PWM) demodulator. Feedback from the plurality of sensors can generate a sensor offset and the PWM demodulator can be varied to reduce the sensor offset to null and provide sensor-to-sensor variations, which are independent of error in the sensor measurements.

In an embodiment, the plurality of sensors can comprise one or more temperature sensors.

In an embodiment, the plurality of sensors can comprise one or more pressure sensors.

In an embodiment, the plurality of sensors can comprise one or more humidity sensors.

In an embodiment, the plurality of sensors can comprise one or more temperature sensors, one or more pressure sensors and/or one or humidity sensors.

In an embodiment, a reference analog signal can be generated with a compensation algorithm and the reference analog signal can be used for zeroing the sensor offset.

In an embodiment, the compensation algorithm can use temperature and humidity sensor values from the sensor measurements to generate the sensor offset.

In an embodiment, an output can be varied in a closed loop to nullify the sensor offset.

In an embodiment, a method of operating a gas sensor system, can involve: receiving sensor measurements from a plurality of sensors; generating a sensor offset from feedback from the plurality of sensors; and varying a pulse width modulation (PWM) demodulator to reduce the sensor offset to null and provide sensor-to-sensor variations independent of error in the sensor measurements.

An embodiment of the method can further involve generating a reference analog signal with a compensation algorithm and using the reference analog signal for zeroing the sensor offset.

In an embodiment of the method, the compensation algorithm can use temperature and humidity sensor values from the sensor measurements to generate the sensor offset.

An embodiment of the method can further involve varying an output in a closed loop to nullify the sensor offset.

In another embodiment, a gas sensor system can include one or more processors and a memory, wherein the memory can store instruction to cause the one or more processors to perform: receiving sensor measurements from a plurality of sensors; generating a sensor offset from feedback from the plurality of sensors; and varying a pulse width modulation (PWM) demodulator to reduce the sensor offset to null and provide sensor-to-sensor variations independent of error in the sensor measurements.

In an embodiment, the instructions can cause the one or more processors to perform generating a reference analog signal with a compensation algorithm and using the reference analog signal for zeroing the sensor offset. In addition, a compensation algorithm can use temperature and humidity sensor values from the sensor measurements to generate the sensor offset.

In an embodiment, the instructions can cause the one or more processors to perform: varying an output in a closed loop to nullify the sensor offset.

BRIEF DESCRIPTION OF THE DRAWINGS

The accompanying figures, in which like reference numerals refer to identical or functionally similar elements throughout the separate views and which are incorporated in and form a part of the specification, further illustrate the present invention and, together with the detailed description of the invention, serve to explain the principles of the present invention.

FIG. 8A illustrates a graph depicting data indicative of method PPM versus time for sample D2 obtained from test results of experiments involving methane gas in a chamber, in accordance with an embodiment;

FIG. 8B illustrates a graph depicting data indicative of method PPM versus time for sample D4 obtained from test results of experiments involving methane gas in a chamber, in accordance with an embodiment;

Identical or similar parts or elements in the figures may be indicated by the same reference numerals.

DETAILED DESCRIPTION

Figures 1, 2:
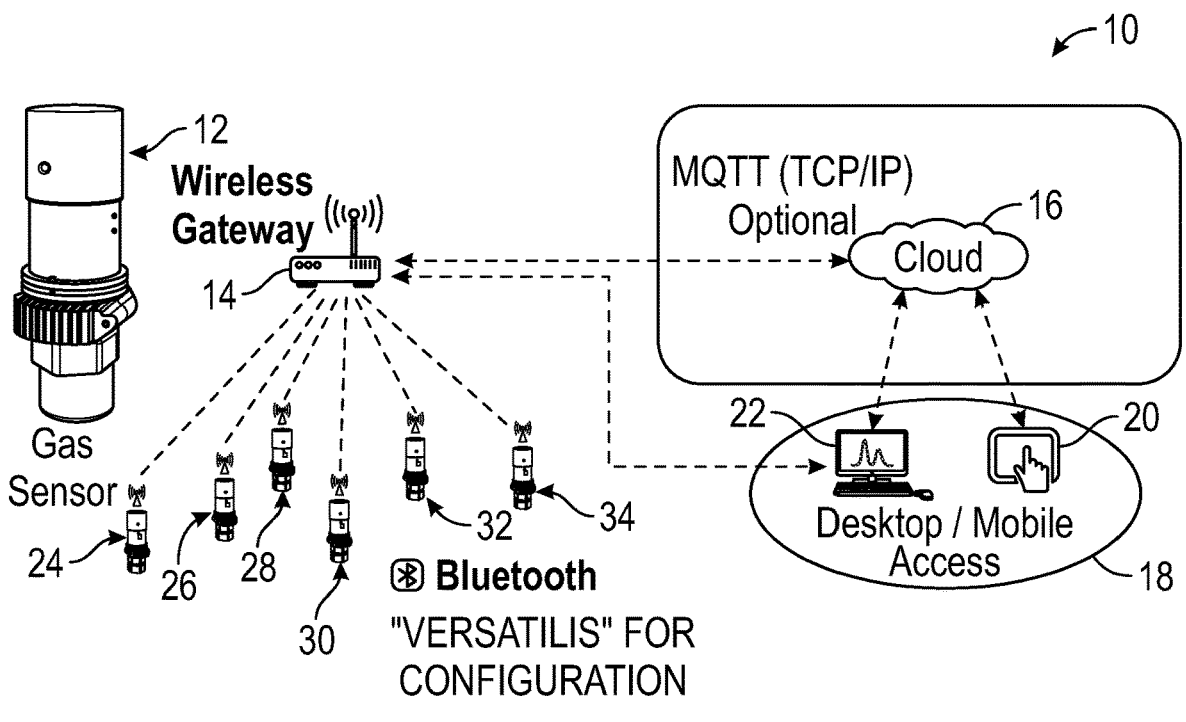
FIG. 1 illustrates a schematic diagram depicting a gas sensor system with dynamic environmental compensation using an auto-calibration method, in accordance with an embodiment.
FIG. 2 illustrates a block diagram of a gas sensor system with dynamic compensation, in accordance with an embodiment.

The particular values and configurations discussed in these non-limiting examples can be varied and are cited merely to illustrate one or more embodiments and are not intended to limit the scope thereof.

Subject matter will now be described more fully hereinafter with reference to the accompanying drawings, which form a part hereof, and which show, by way of illustration, specific example embodiments. Subject matter may, however, be embodied in a variety of different forms and, therefore, covered or claimed subject matter is intended to be construed as not being limited to any example embodiments set forth herein; example embodiments are provided merely to be illustrative. Likewise, a reasonably broad scope for claimed or covered subject matter is intended. Among other issues, subject matter may be embodied as methods, devices, components, or systems. Accordingly, embodiments may, for example, take the form of hardware, software, firmware, or a combination thereof. The following detailed description is, therefore, not intended to be interpreted in a limiting sense.

Throughout the specification and claims, terms may have nuanced meanings suggested or implied in context beyond an explicitly stated meaning. Likewise, phrases such as "in an embodiment" or "in one embodiment" or "in an example embodiment" and variations thereof as utilized herein may or may not necessarily refer to the same embodiment and the phrase "in another embodiment" or "in another example embodiment" and variations thereof as utilized herein may or may not necessarily refer to a different embodiment. It is intended, for example, that claimed subject matter include combinations of example embodiments in whole or in part.

In general, terminology may be understood, at least in part, from usage in context. For example, terms, such as "and," "or," or "and/or," as used herein may include a variety of meanings that may depend, at least in part, upon the context in which such terms are used. Generally, "or" if used to associate a list, such as A, B, or C, is intended to mean A, B, and C, here used in the inclusive sense, as well as A, B, or C, here used in the exclusive sense. In addition, the term "one or more" as used herein, depending at least in part upon context, may be used to describe any feature, structure, or characteristic in a singular sense or may be used to describe combinations of features, structures, or characteristics in a plural sense. Similarly, terms such as "a," "an," or "the," again, may be understood to convey a singular usage or to convey a plural usage, depending at least in part upon context. Furthermore, the term "at least one" as used herein, may refer to "one or more." For example, "at least one widget" may refer to "one or more widgets."

In addition, the term "based on" may be understood as not necessarily intended to convey an exclusive set of factors and may, instead, allow for existence of additional factors not necessarily expressly described, again, depending at least in part on context.

As will be discussed in greater detail below, embodiments can relate to a gas sensor system and a method of operating the gas sensor system. An embodiment may include a group of sensors and a microcontroller that can receive sensor measurements from the group of sensors. Feedback from the group of sensors can generate a sensor offset and a pulse width modulation (PWM) demodulator can be varied to reduce the sensor offset to null and provide sensor-to-sensor variations, which are independent of error in the sensor measurements.

FIG. 1 illustrates a schematic diagram depicting a gas sensor system 10 with dynamic environmental compensation using an auto-calibration method, in accordance with an embodiment. The gas sensor system 10 shown in FIG. 1 includes a group of gas sensors (e.g., field devices) including a gas sensor 24, a gas sensor 26, a gas sensor 28, a gas sensor 30, a gas sensor 32, and a gas sensor 34, which can communicate wirelessly with a wireless gateway 14. Note that a large view of such gas sensors is depicted in FIG. 1 as gas sensor 12.

The wireless gateway can communicate bidirectionally with a cloud-based network 16, which in turn can communicate bidirectionally with a desktop computer 22 and/or mobile computing device 20 (e.g., a tablet computing device, smartphone, etc.), which are represented as computing devices 18 in FIG. 1. Note that each of the gas sensors shown in FIG. 1 can communicate wirelessly and bidirectionally with the wireless gateway 14 via Bluetooth® communications and/or a Versalitis™ arrangement. Examples of a Versalitis TM arrangement are described at the following link: process.honeywell.com/us/en/initiative/versatilis, the content of which is incorporated herein by reference in its entirety.

FIG. 2 illustrates a block diagram of a gas sensor system 40 with dynamic compensation, in accordance with an embodiment. The gas sensor system 40 includes a MOX/Pellistor/nondispersive infrared sensor (NDIR)/electrochemical sensor 42 that can output data, which can be input to a buffer 46 that in turn can output data, which can be input to amplifier 48 and an analog-to-digital converter (ADC) 50. Output from the amplifier 48 can be provided as input to the ADC 50, which in turn can output data that can be provided as input to a microcontroller 52. A temperature and humidity sensor 54 can output sensor measurement signals/data, which are input to the microcontroller 52 in addition to the data output from the ADC 50.

Note that the term "pellistor" as utilized herein relates to a solid state device that can be used to detect gases, which are either combustible or which can possess a significant difference in thermal conductivity to that of air. The word "pellistor" is a combination of pellet and resistor.

The gas sensor system 40 can further include a digital-to-analog converter (DAC)/pulse width modulation (PWM) demodulator/filter unit 56, which can receive data output from the microcontroller 52. Data output from the DAC/PWM demodulator/filter unit 56 can be provided as input to a buffer 58, which in turn can output data that can be input to the amplifier 48 and also provided as a compensated signal to the ADC 50. The data or signal output from the microcontroller 52 to the DAC/PWM demodulator/filter unit 56 can be a PWM signal that is proportional to the compensation signal output from the buffer 58.

Figure 3:
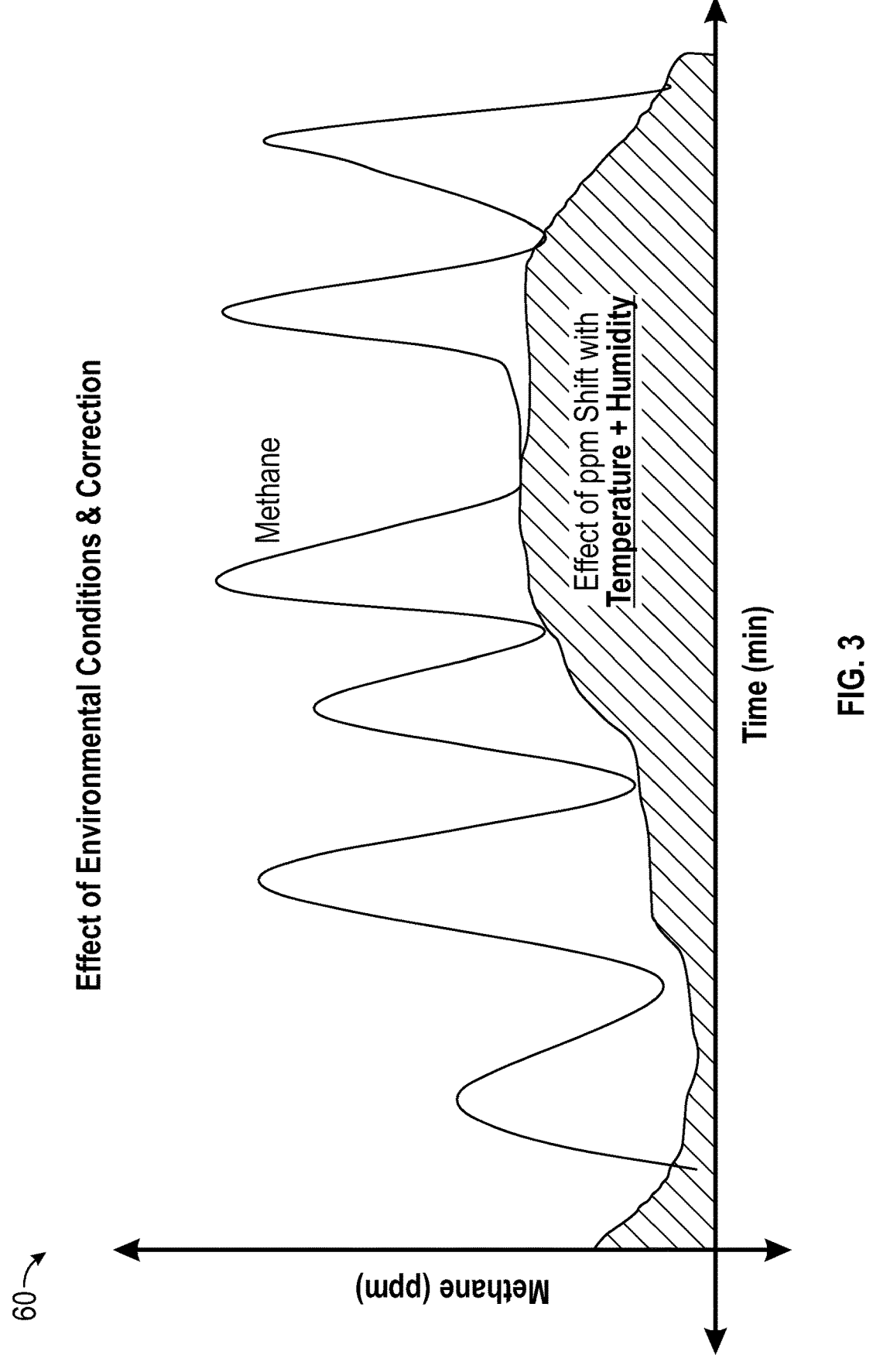
FIG. 3 illustrates a graph depicting the effects of environmental conditions and a correction in accordance with an embodiment.

FIG. 3 illustrates a graph 60 depicting the effects of environmental conditions and a correction in accordance with an embodiment. Graph 60 shown in FIG. 3 plots methane (ppm) versus time (min) to track methane and the effect of ppm shift with temperature plus humidity.

Figure 4:
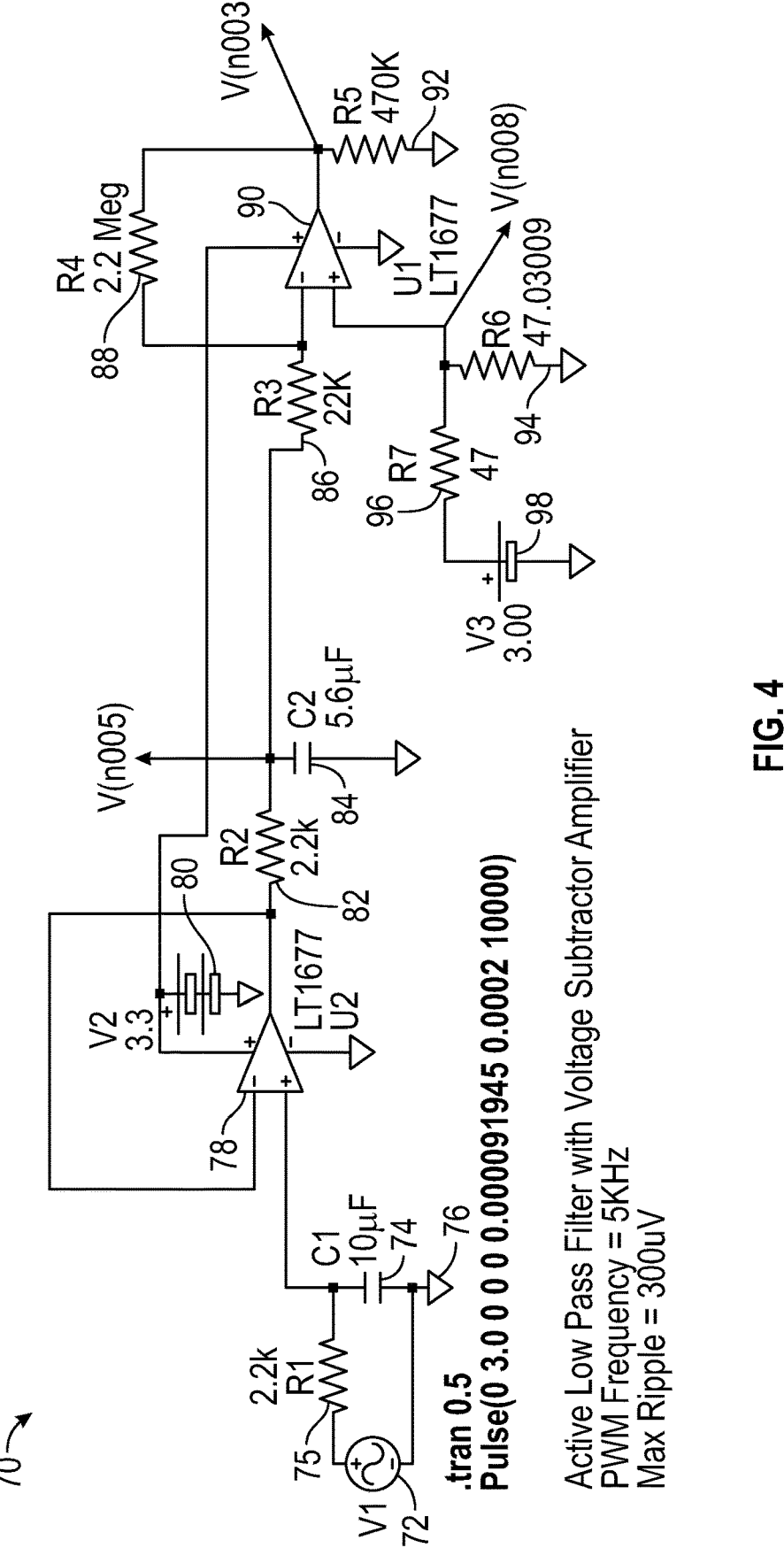
FIG. 4 illustrates a schematic diagram of a circuit, which can be implemented in accordance with an embodiment.

FIG. 4 illustrates a schematic diagram of a circuit 70, which can be implemented in accordance with an embodiment. The circuit 70 can function as an active low pass filter with a voltage subtractor amplifier. Note that in the configuration shown in FIG. 4, the PWM frequency is 5 KHz with a maximum ripple of 300 uV. Note that the numerical values disclosed herein and shown in the various figures accompanying this disclosure should not be considered as limiting features of the embodiments. Rather, these values and parameters are provided herein for illustrative and exemplary purposes only.

The circuit 70 includes a power source 72 that can be tied electronically to ground 76 and to a resistor 75. The power source 72 and the resistor 75 are located in parallel with a capacitor 74. The resistor 75 and the capacitor 74 are in turn connected electronically to a positive input of operational amplifier 78. A negative input of the operational amplifier 78 is electronically connected to a resistor 82. The operational amplifier 78 is also tied to ground and to a voltage source 80. The resistor 82 is further connected electronically to a capacitor 84 and a resistor 86. The resistor 86 is tied electronically to a resistor 88 and a negative input of an operational amplifier 90. Output from the operational amplifier 90 is tied electronically to a resistor 92 and to the resistor 88. A positive input of the operational amplifier 90 is tied electronically to a resistor 94 and a resistor 96. A voltage source 98 is tied electronically to the resistor 96.

Based on the foregoing it can be appreciated that a hardware and firmware based method of dynamic compensation for a gas sensor can be implemented, which can include a reference analog signal generated using a compensation algorithm. The reference analog signal can be used for zeroing the sensor offset. The aforementioned compensation algorithm can use the temperature and humidity sensor values to generate the sensor offset. Based on the output from the compensation algorithm, the PWM can be varied in a close loop to basically nullify the sensor offset.

Figure 5:
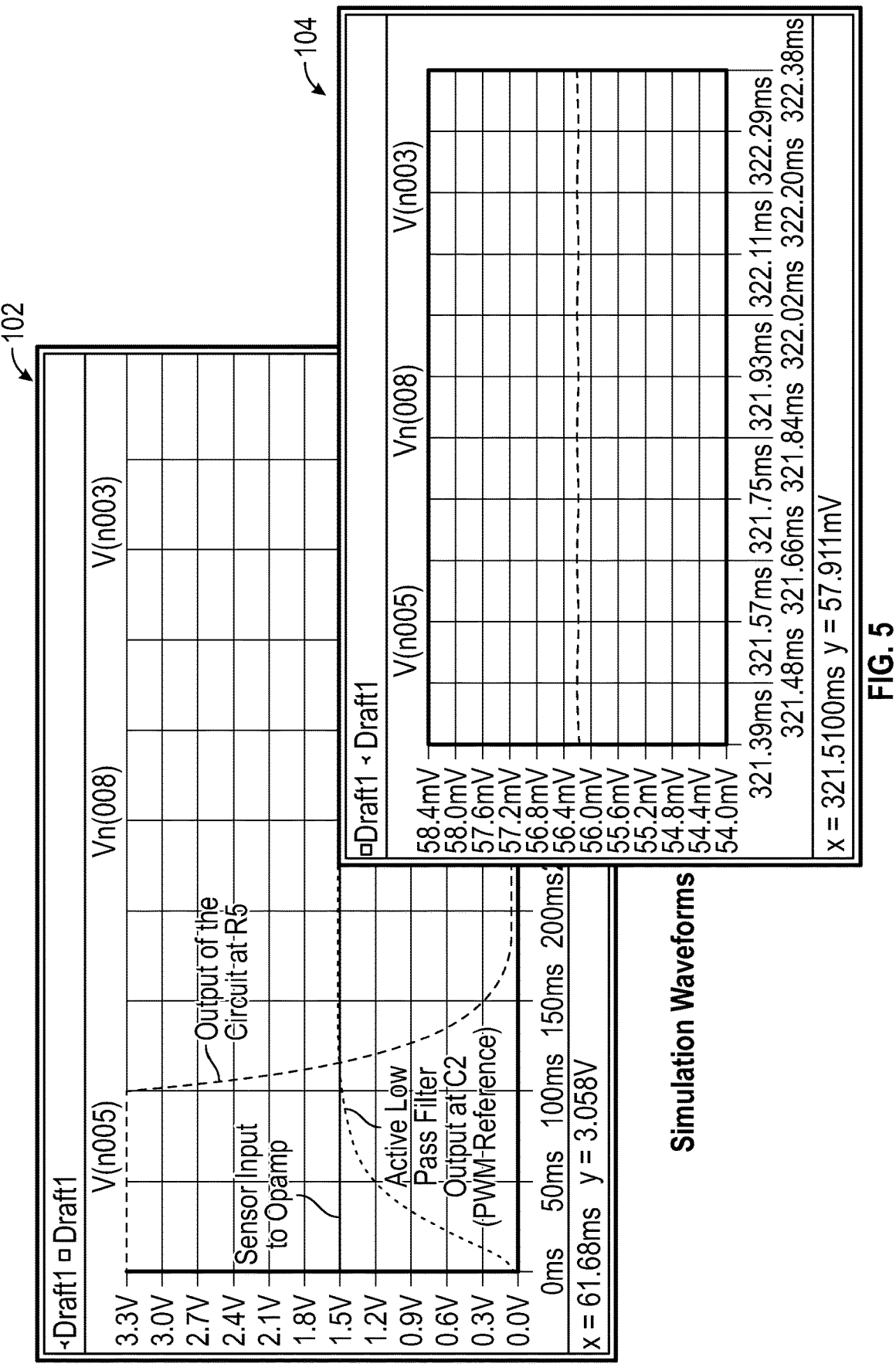
FIG. 5 illustrates graphs depicting dynamic compensation simulations waveforms in accordance with an embodiment.

FIG. 5 illustrates graphs 102 and 104 depicting dynamic compensation simulations waveforms in accordance with an embodiment. Graph 102 depicts the output of the circuit 70 shown in FIG. 4 at resistor 92 (also identified as R5 in FIG. 4). Graph 102 also indicates sensor input to the operational amplifier(s) shown in FIG. 4 and an active low pass filter output at capacitor 84 (also identified as C2 in FIG. 4) (PWM reference). Graph 104 depicts simulations waveforms for example use cases.

Figures 6A, 6B:
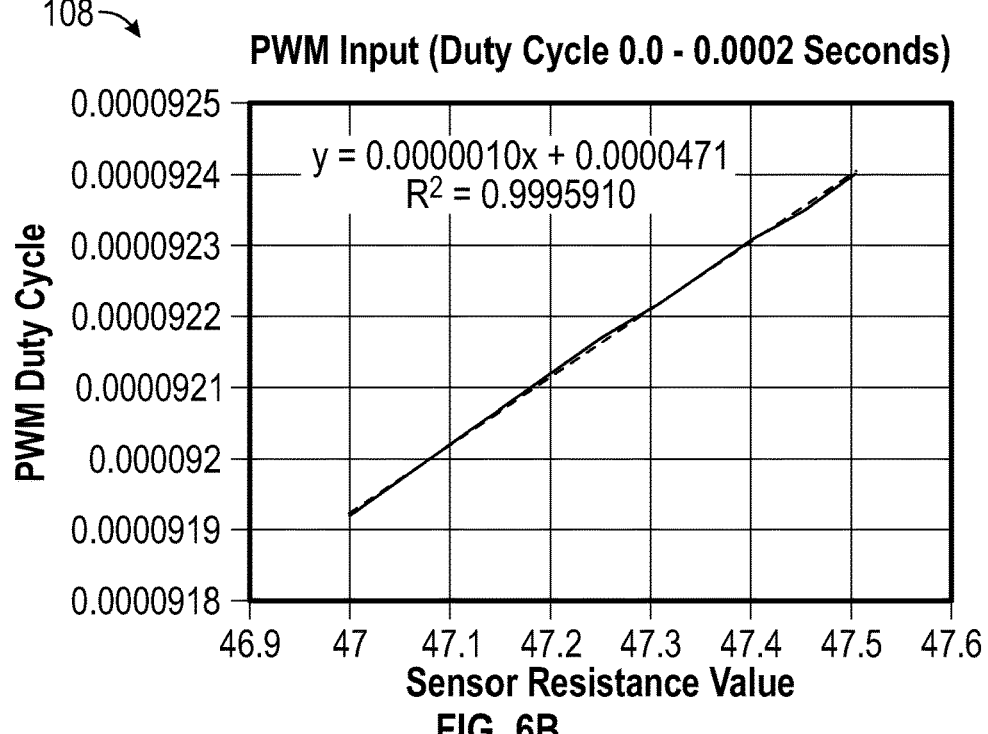
FIG. 6A illustrates a table with data obtained from an example simulation analysis, in accordance with an embodiment.
FIG. 6B illustrates a graph of data indicative of PWM duty cycle versus sensor resistance values in an example simulation analysis, in accordance with an embodiment.

FIG. 6A and FIG. 6B respectively illustrate a table 106 and a graph 108 of an example simulation analysis, in accordance with an embodiment. The table 106 shown in FIG. 6A includes values indicative of, for example, PPM change, voltage change with ppm (V) and final voltage change data from the sensor(s). The table 106 also lists resistance values, PWM input and output data. The graph 108 plots the data shown in table 106 to provide PWM input data (for a duty cycle of 0.0 seconds to 0.0002 seconds)

Figure 7A:
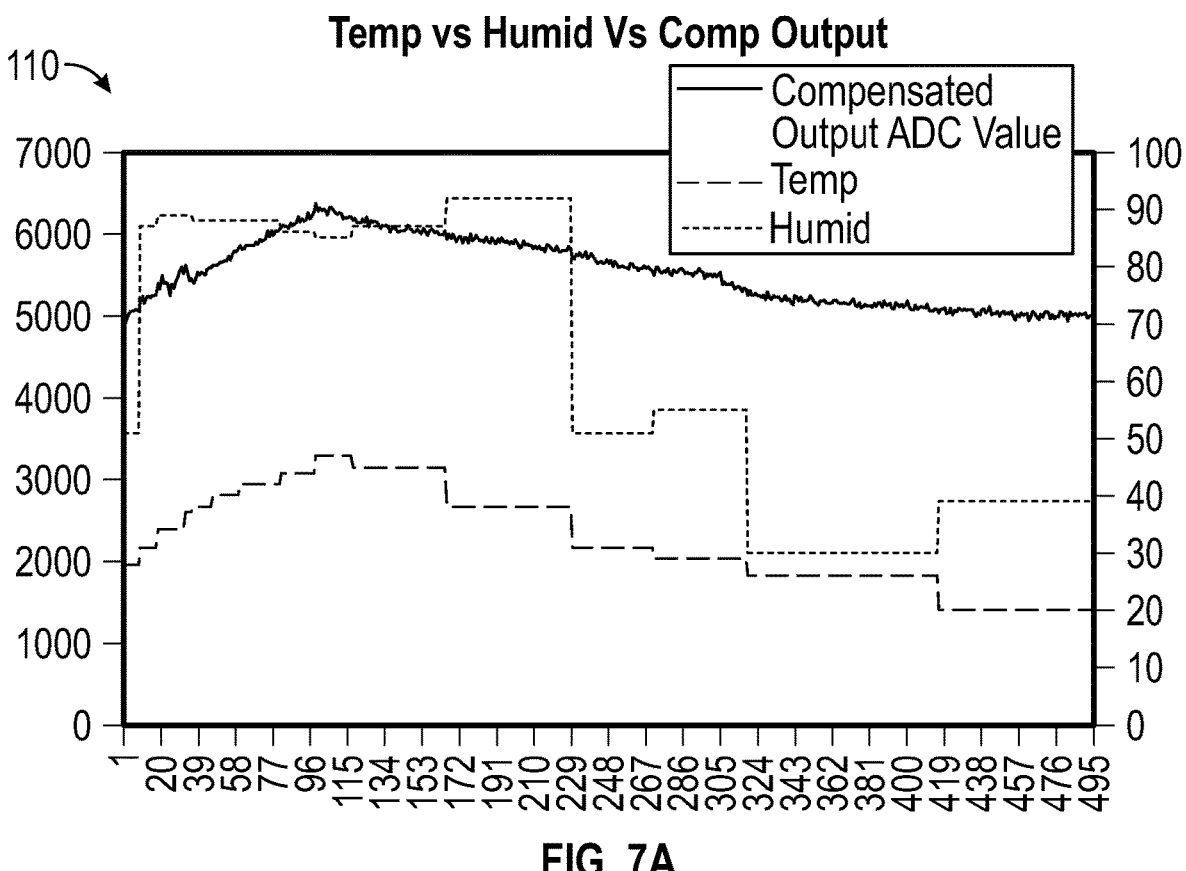
FIG. 7A illustrates a graph of temperature versus humidity versus compensated output data obtained from test results of experiments with methane gas injected, in accordance with an embodiment.
Figure 7B:
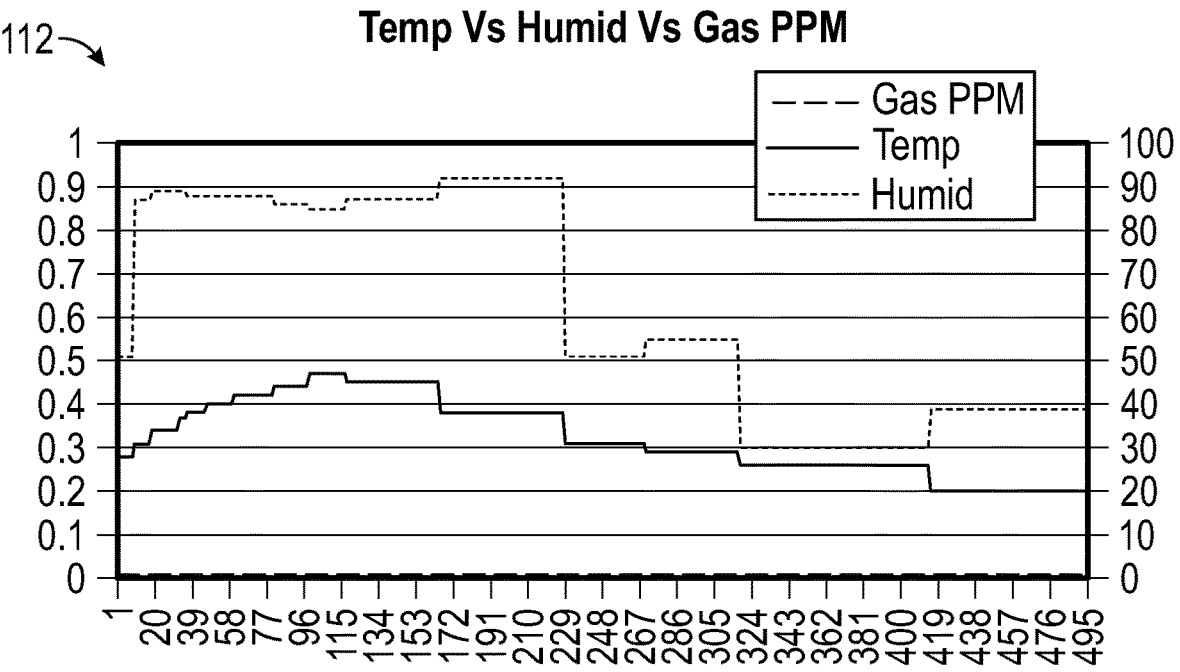
FIG. 7B illustrates a graph of temperature versus humidity versus gas PPM (Parts Per Million) data obtained from test results of experiments with methane gas injected, in accordance with an embodiment.
Figure 7C:
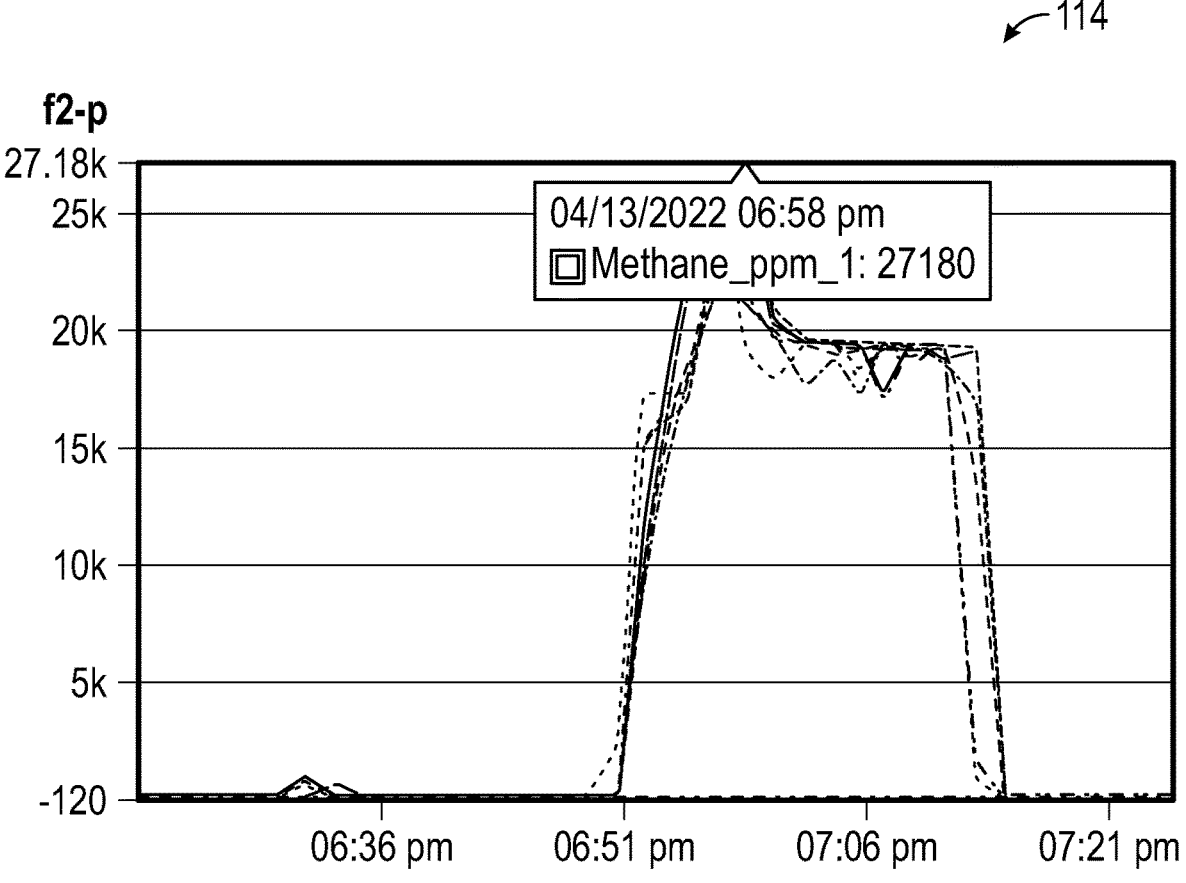
FIG. 7C illustrates a graph of depicting test results of experiments with methane gas injected, in accordance with an embodiment.
Figure 8C:
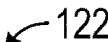
FIG. 8C illustrates a graph depicting data indicative of method PPM versus time for sample D13 obtained from test results of experiments involving methane gas in a chamber, in accordance with an embodiment.
Figure 8C:
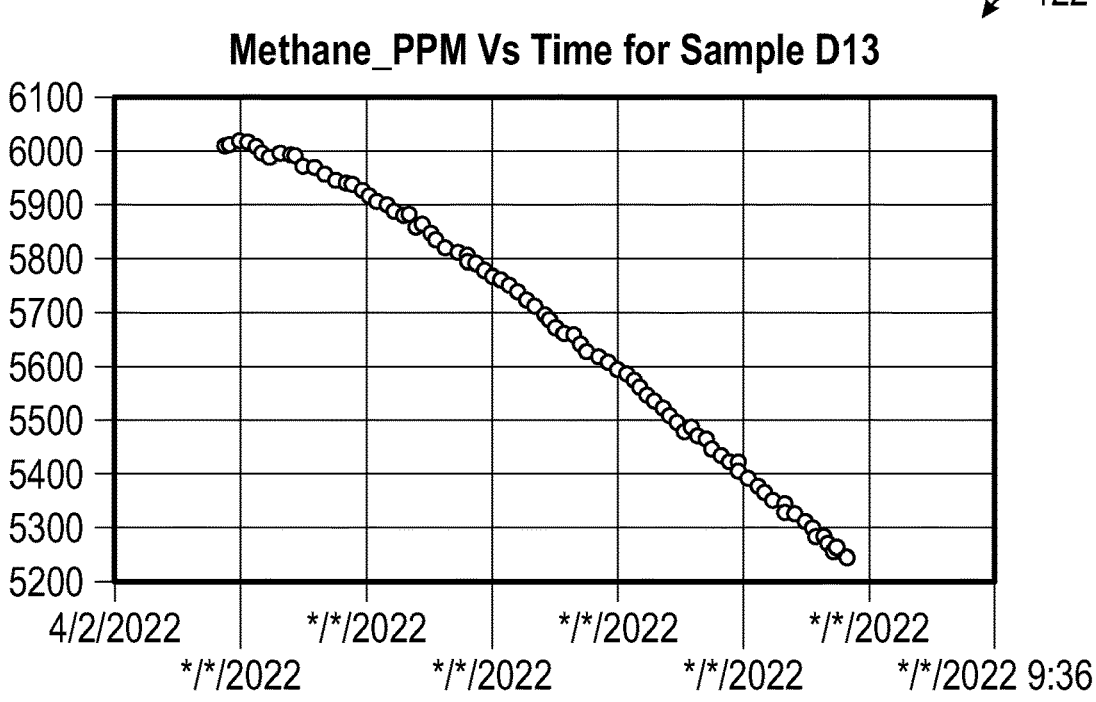
Figure 8D:
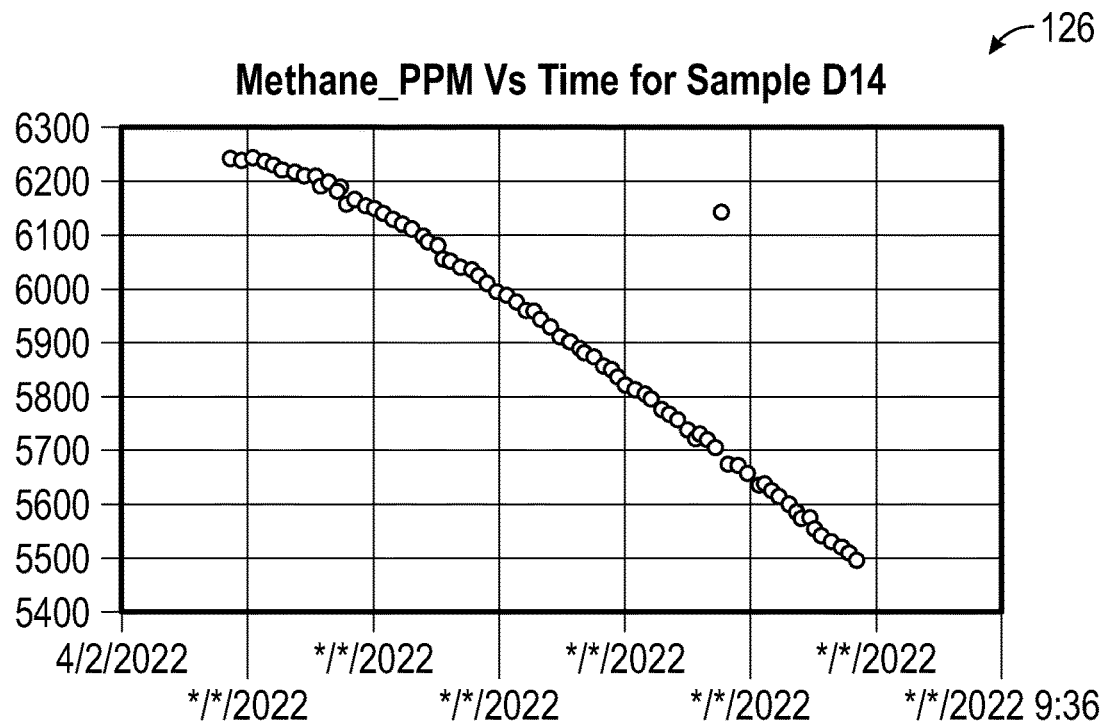
FIG. 8D illustrates a graph depicting data indicative of method PPM versus time for sample obtained from test results of experiments involving methane gas in a chamber, in accordance with an embodiment.

FIG. 7A, FIG. 7B, and FIG. 7C respectively illustrate graphs 110, 112, and 114 depicting test results of experiments with methane gas injected, in accordance with an embodiment. Graph 110 illustrates data indicative of temperature versus humidity versus compensation output. Graph 112 illustrates data involve temperature versus humidity versus gas PPM. Graph 114 depicts data involve methane PPM.

FIG. 8A, FIG. 8B, FIG. 8C, and FIG. 8D respectively illustrate graphs 120, 122, 124, and 126 depicting test results of experiments involving methane gas in a chamber, in accordance with an embodiment. Each of the graphs 120, 122, 124, and 126 depicts data indicative of methane PPM versus time.

Figure 9A:
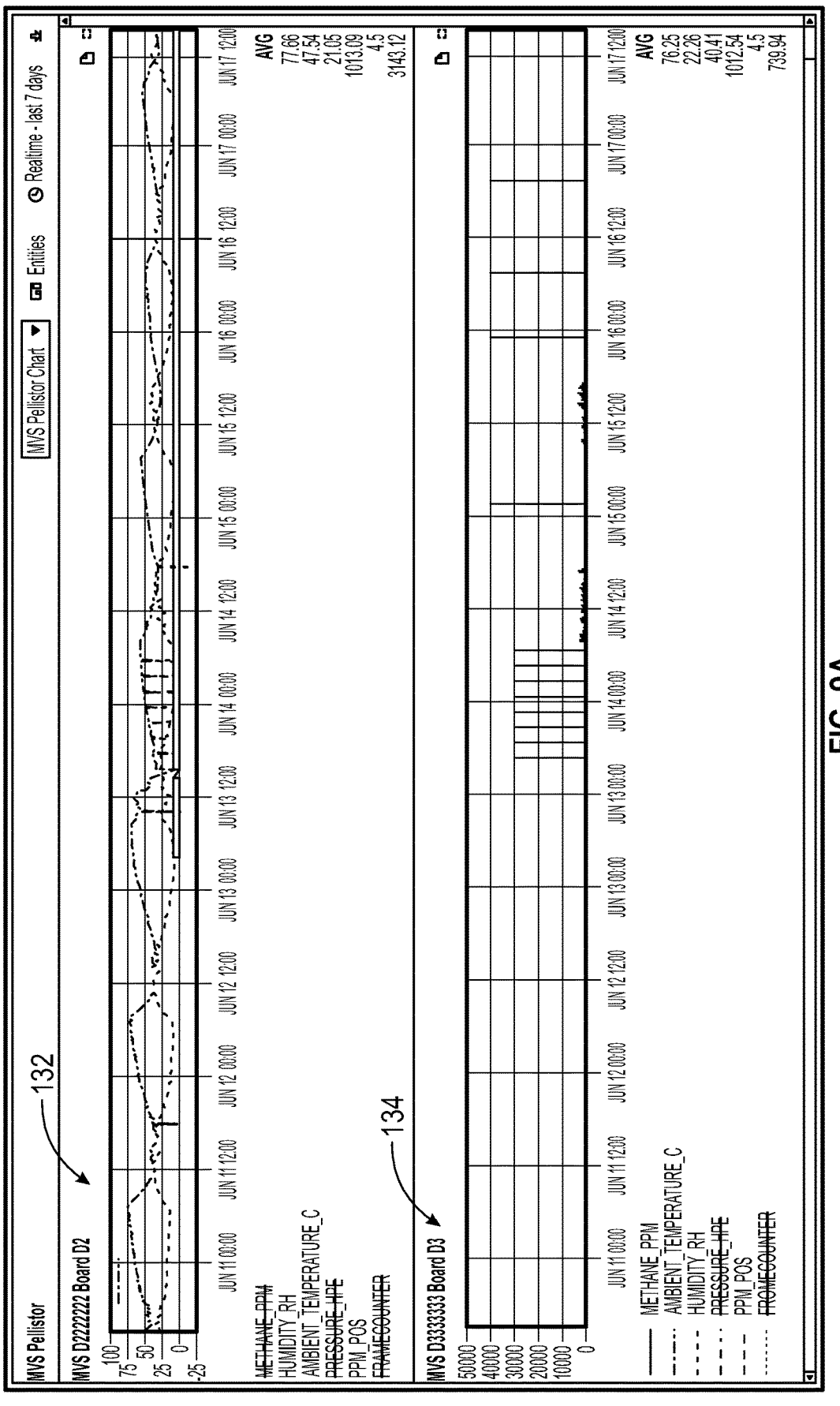
FIG. 9A illustrate graphs depicting test results related to outdoor methane plumes leak detection, in accordance with an embodiment.
Figure 9B:
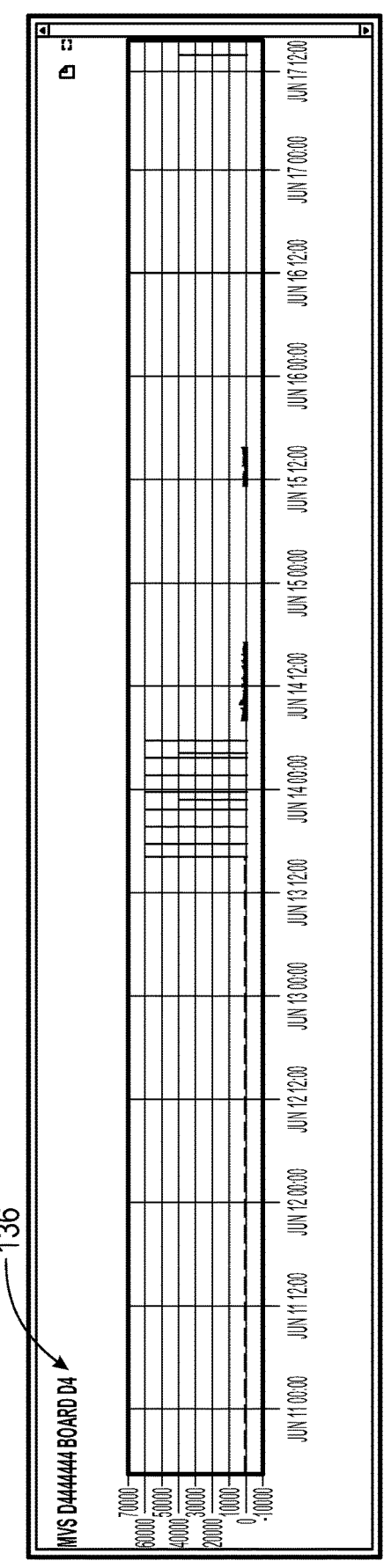
FIG. 9B illustrate a graph depicting test results related to outdoor methane plumes leak detection, in accordance with an embodiment.
Figure 10A:
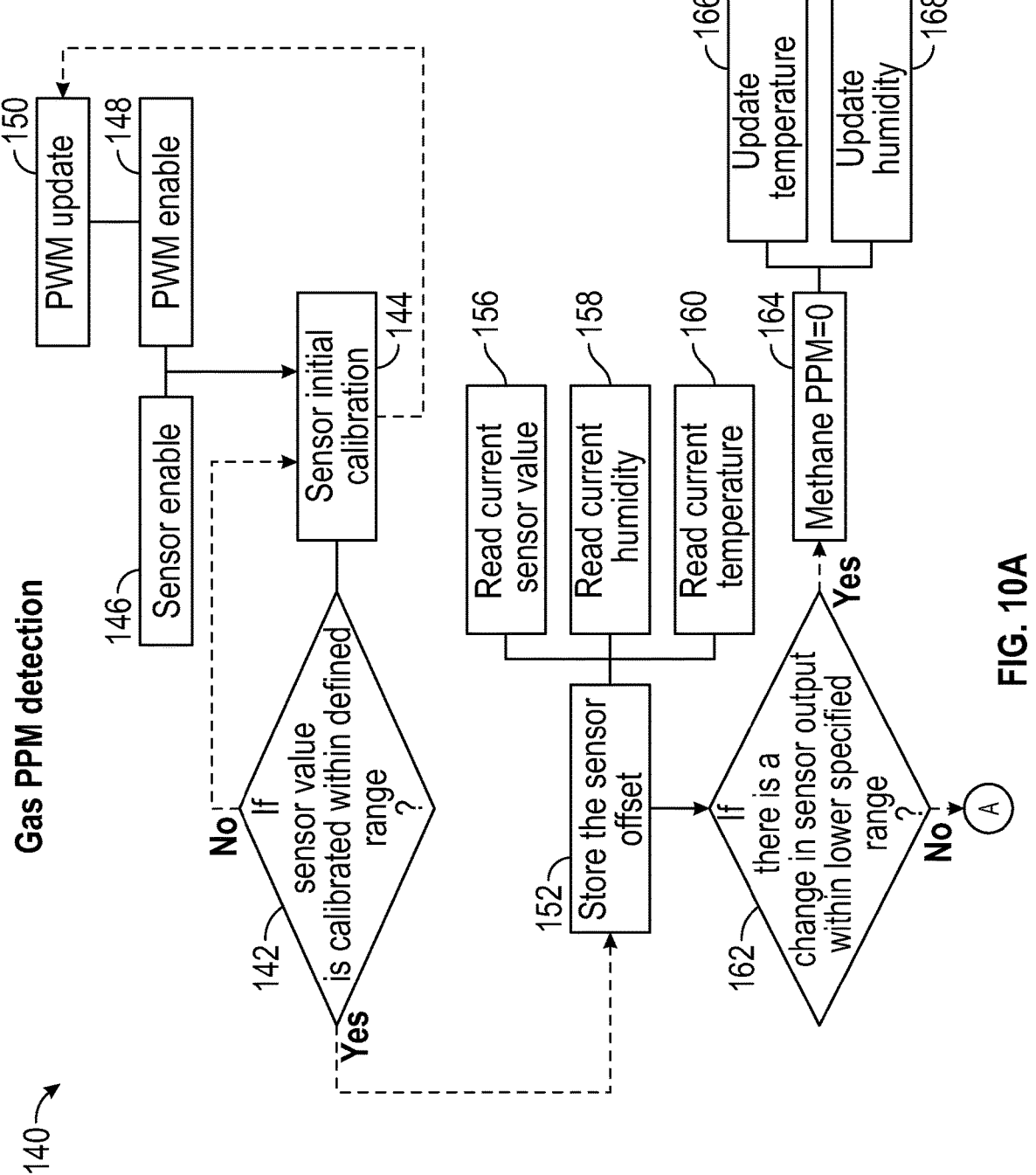
FIG. 10A illustrates a flow chart of operations depicting logical operational steps of a gas sensing method of dynamic environmental compensation using auto-calibration, in accordance with an embodiment.
Figure 10B:
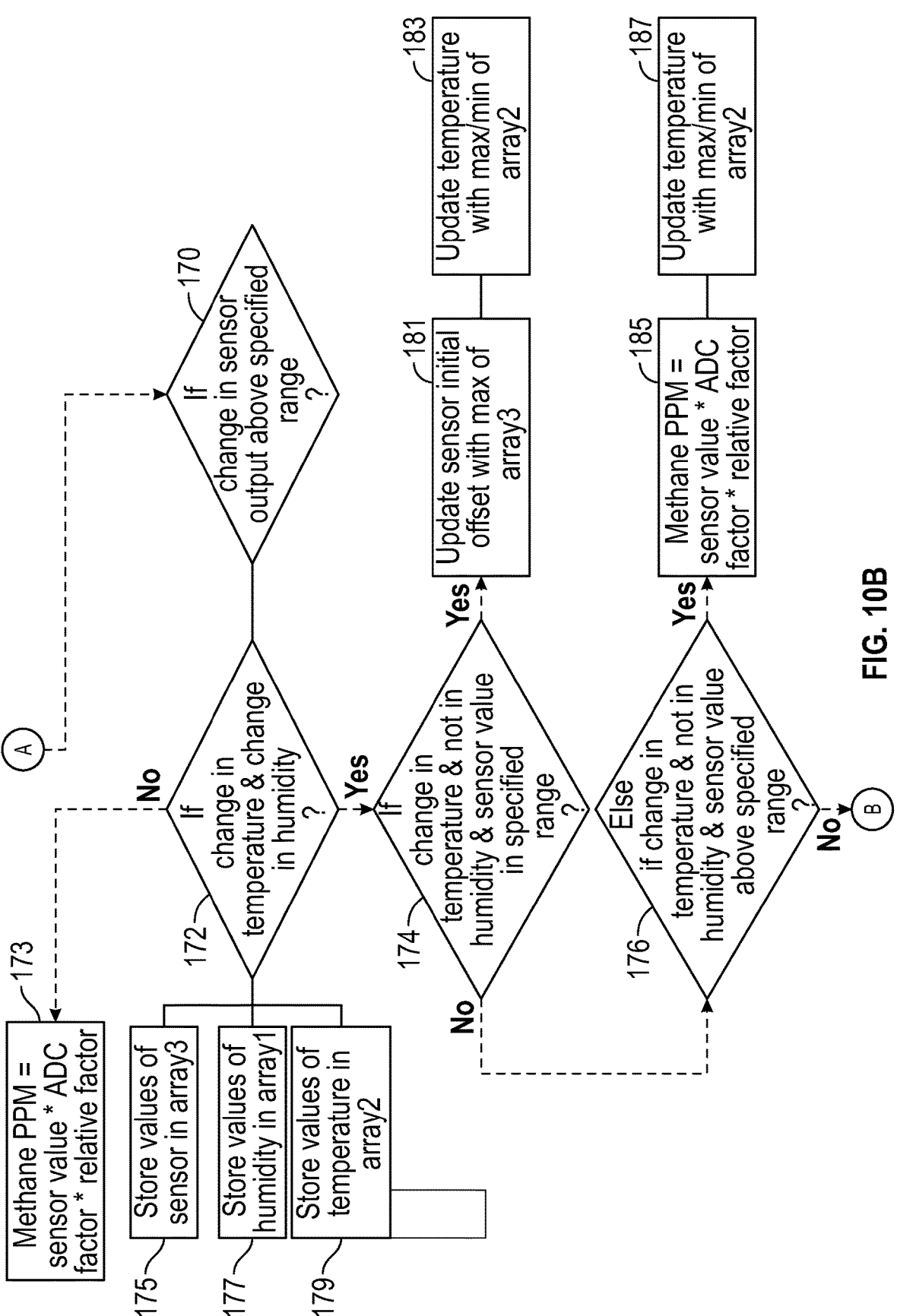
FIG. 10B illustrates continued operational steps of the flow chart of operations depicted in FIG. 10A, in accordance with an embodiment.
Figure 10C:
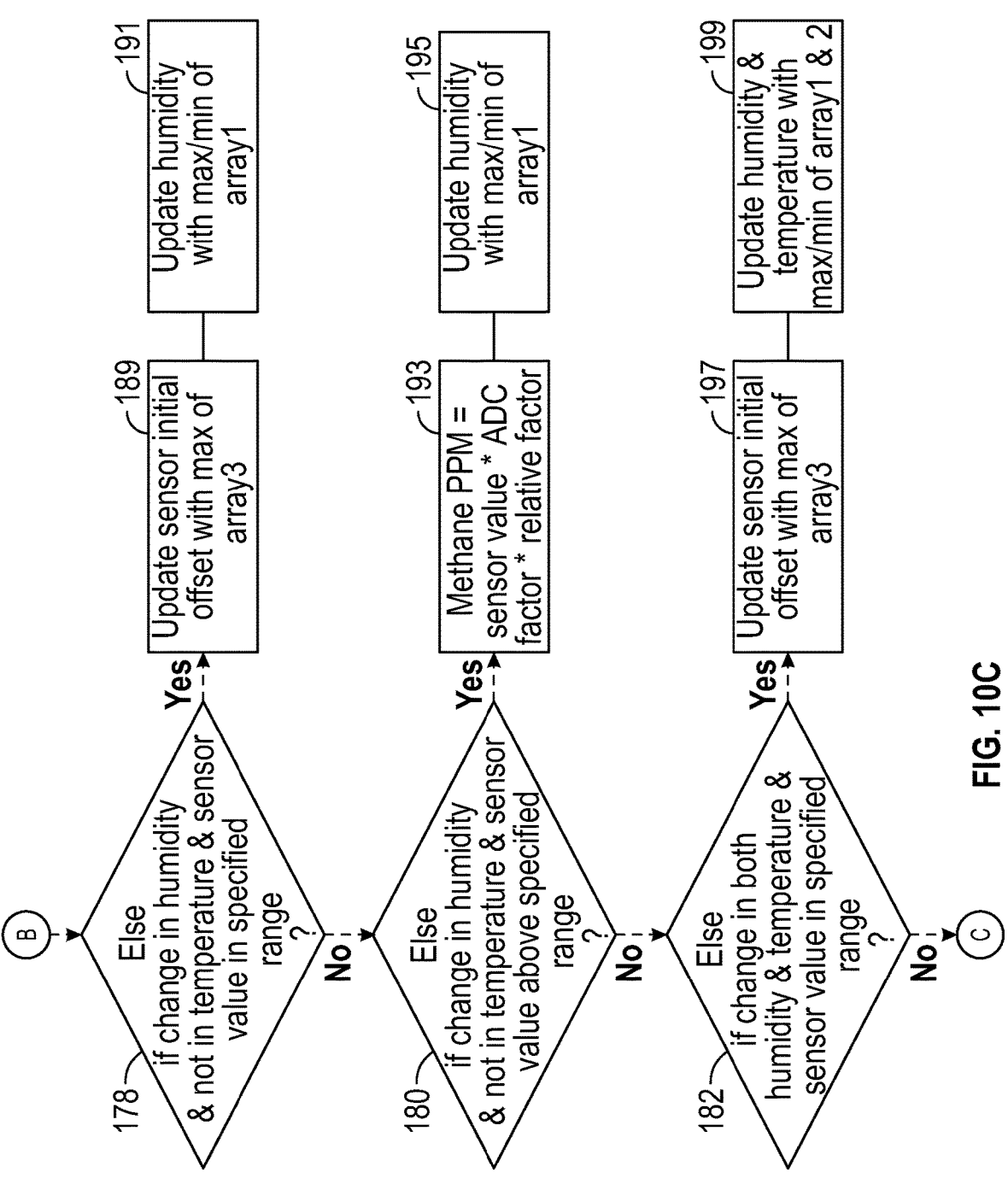
FIG. 10C illustrates continued operational steps of the flow chart of operations depicted in FIG. 10A, FIG. 10B, and FIG. 10C, in accordance with an embodiment.
Figure 10D:
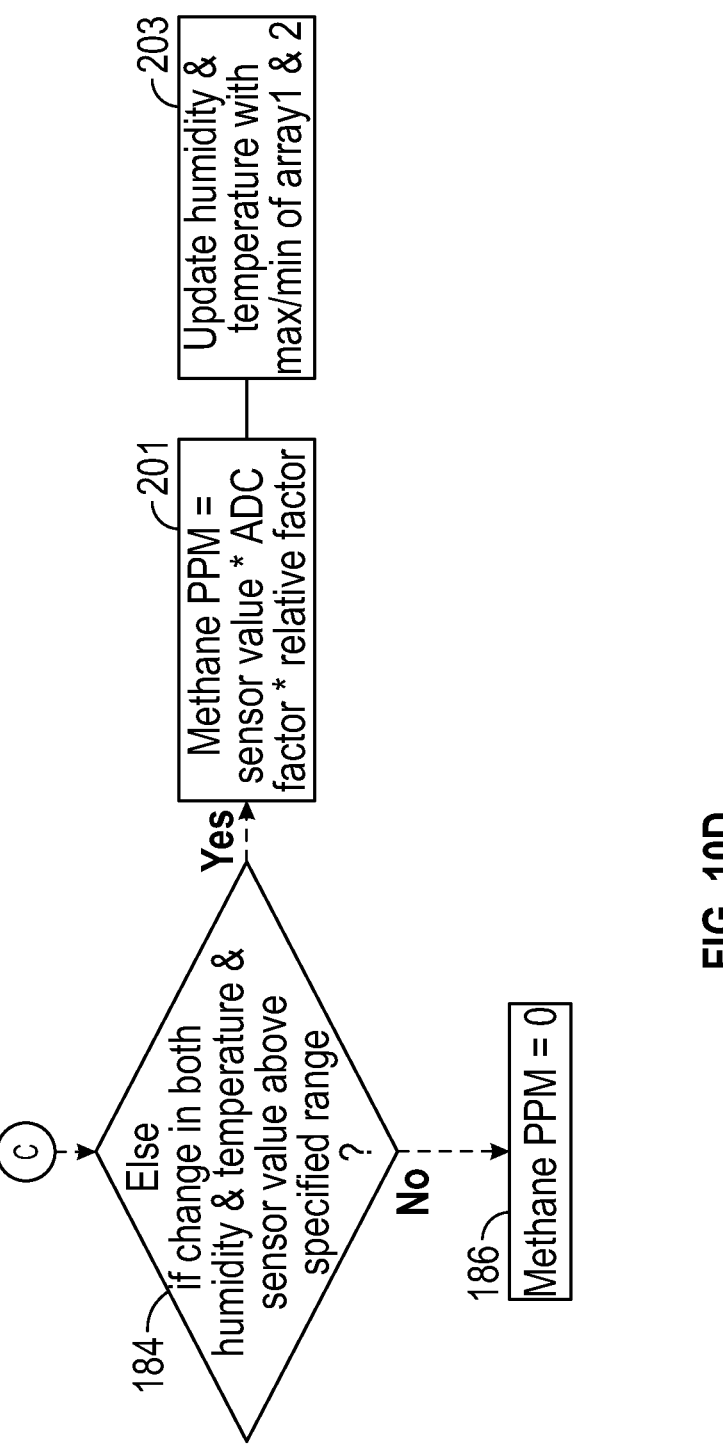
FIG. 10D illustrates continued operational steps of the flow chart of operations depicted in FIG. 10A, FIG. 10B, and FIG. 10C, in accordance with an embodiment.

FIG. 9A, FIG. 9B, and FIG. 9C respectively illustrate graphs 132, 134, and 136 depicting test results related to outdoor methane plumes leak detection, in accordance with an embodiment. The example data contained in graphs 132, 134, and 136 relate to sensor measurements obtained from a pellistor.

FIG. 10A, FIG. 10B, FIG. 10C and FIG. 10D illustrate a flow chart of operations depicting logical operational steps of a gas sensing method 140 of dynamic environmental compensation using auto-calibration, in accordance with an embodiment. The method 140 can be implemented for gas PPM detection. As shown at decision block 142, a test can be implemented to determine if a sensor value has been calibrated in an initial calibration with a defined range. If so, then an initial sensor calibration operation can be implemented as shown at block 144. If not, the operation depicted at block 144 can also be implemented. Then, as indicated at block 148, a PWM enable operation can be implemented. The sensor can be then enabled, as shown at block 146.

Thereafter, as shown at block 156, the current sensor can be read. In addition, as illustrated at block 158, the current humidity can be read. Furthermore, as shown at block 160, the current temperature can be read. If a 'yes' response occurs with respect to the operation depicted at block 142, then the sensor offset occurs as shown at block 152.

Then, following processing of the operation shown at block 152 including the operations depicted at blocks 156, 158, and 160, a test can be performed if there has been a change in the sensor output and within a lower specified range, as illustrated at decision block 162. If the answer is "yes," then the methane PPM=0 as shown at block 164. The temperature can be then updated as shown at block 166 and the humidity updated as depicted at block 168. If the answer is "no," then as shown at decision block 170, a test can be performed to determine if there has been a change in the sensor output above a specified range Then, as shown at decision block 172, a test can be performed to determine if there has been a change in temperature and humidity. As shown at block 175, values of the sensor can be stored in Array 3. In addition, as depicted at block 177, values of humidity can be stored in Array 1. Furthermore, as described at block 179, values of temperature can be stored in Array 2.

Following processing of the operation shown at decision block 172, a test can be performed to determine if a change has occurred in temperature and not in humidity and the sensor value is in a specified change, as indicated at decision block 174. If the answer is "yes" with respect to the operation shown at decision block 174, an operation can be implemented to update the sensor initial offset with a maximum of Array 3. Then, as shown at block 183, a step or operation can be implemented to update the temperature with the max/min value(s) of Array 2.

If the answer is "no" with respect to the operation shown at decision block 174, then as depicted at decision block 176, a test can be performed to determine if a change in temperature but not humidity has occurred, and furthermore if the sensor value is above a specified range. If the answer is "yes" with respect to the operation shown at block 176, the following equation can be implemented as shown at block 185: Methane PPM=Sensor value*ADC factor*relative factor.

Then, as shown at block 187, temperature can be updated with max/min of Array 1. If the answer is "yes" with respect to the operation shown at block 178, then as shown at block 189, the sensor initial offset can be updated with the maximum of Array 3. The humidity can be then updated with the max/min of Array 1, as shown at block 191. If the answer is "no" with respect to the operation shown at block 178, then a test can be performed as indicated at block 180 to determine if a change in humidity but not in temperature has occurred and furthermore, if the sensor value is above a specified range. If the answer is "yes" with respect to the operation shown at block 180, then as indicated at block 193, the following equation can be implemented: Methane PPM=Sensor value*ADC factor*relative factor. Next, as depicted at block 195, humidity can be updated with the max/min of Array 1.

If the answer is "no" with respect to the operation depicted at decision block 180, then as shown at decision block 182, a test can be performed to determine if a change has occurred in both humidity and temperature and furthermore that the sensor value is in a specified range. If the answer is "yes" with respect to the operation shown at decision block 182, then as shown at block 197, the sensor initial offset can be updated with the maximum of Array 3. Then, as illustrated at block 199, humidity and temperature can be updated with the max/min of Array 1 and Array 2.

If the answer is "no" with respect to the operation depicted at decision block 182, a test can be performed as shown at block 184 to determine if a change in humidity and temperature has occurred, along with a change in the sensor value above a specified range. If the answer is "yes" with respect to the operation shown at decision block 184, then the following equation can be implemented as indicated at block 201: Methane PPM=Sensor value*ADC factor*relative factor. Then, as shown at block 203, humidity and temperature can be updated with the max/min of Array 1 and Array 2. If the answer is "no" with respect to the operation depicted at decision block 184, then Methane PPM=0.

The method 140 shown in FIG. 10 along with the features discussed with respect to the other figures, can solve the problems discussed earlier and associated with conventional gas sensor signal conditioning, processing, and compensation. The unique gas sensor signal conditioning approach of method 10 can, for example, increase the signal strength with a high signal to noise ratio (SNR), thereby enhancing gas sensor sensitivity and low level gas leak detection capabilities. This novel auto calibration and the previously discussed dynamic compensation hardware and associated algorithm can eliminate the need for special characterization and calibration process in the production of each sensor.

This dynamic compensation method 140 can utilize the live environmental sensor data to compensate the errors and enhance the accuracy of the sensing. The auto calibration and dynamic compensation combination disclosed herein can eliminate the need for conventional look-up tables or stored calibration coefficient methods and can also eliminate the environmental effects, and long term drift for precision gas detection. A smart adaptive sensor platform as disclosed herein can perform a cycle by cycle correction to protect the sensor degradation and adverse effects such as false positives or non-responsive results.

The novel dynamic compensation and auto calibration method 140 can be easily adapted to any type of gas sensing technology thereby making the product more versatile. The disclosed gas sensor system/device can work on low power because the unique method 140 makes the product portable and effectively an internet-of-things (IoT) device. The cost of the gas leak detector solution will be cheaper compared to commercially available solutions in the market because the device/system does not require special characterization and/or calibration processes in production and furthermore, does not require the use of a high-accurate transducer. The auto calibration method 140 can use various conditions to cancel out the effects of environmental effects. This means that the method 140 can perform dynamic compensation/correction for every measurements (cycle by cycle) by checking the rate of output rise slope.

The embodiments can resolve numerous field-related problems, which renders the disclosed approach more robust and cheaper than conventional devices/methods. In addition, there is no need for frequent field calibration and replacement of a sensor transducer/capsule, thereby rendering the solution(s) maintenance free. The embodiments can also align with sustainability growth initiatives in industry because the accurate gas leak detection solution offered by the embodiments can help to meet global sustainability goals.

In the above description, specific details of various embodiments are provided. However, some embodiments may be practiced with less than all of these specific details. In other instances, certain methods, procedures, components, structures, and/or functions are described in no more detail than to enable the various embodiments of the invention, for the sake of brevity and clarity.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

It should also be noted that at least some of the operations for the methods described herein may be implemented using software instructions stored on a computer useable storage medium for execution by a computer. As an example, an embodiment of a computer program product includes a computer useable storage medium to store a computer readable program.

The computer-useable or computer-readable storage medium can be an electronic, magnetic, optical, electromagnetic, infrared, or semiconductor system (or apparatus or device). Examples of non-transitory computer-useable and computer-readable storage media include a semiconductor or solid state memory, magnetic tape, a removable computer diskette, a random access memory (RAM), a read-only memory (ROM), a rigid magnetic disk, and an optical disk. Current examples of optical disks include a compact disk with read only memory (CD-ROM), a compact disk with read/write (CD-R/W), and a digital video disk (DVD). A memory such as described above may store instructions that can cause one or more processors to perform steps and operations such as those of the method 140.

Alternatively, embodiments may be implemented entirely in hardware or in an implementation containing both hardware and software elements. In embodiments which use software, the software may include but is not limited to firmware, resident software, microcode, etc.

Although specific embodiments of the invention have been described and illustrated, the invention is not to be limited to the specific forms or arrangements of parts so described and illustrated. The scope of the invention is to be defined by the claims appended hereto and their equivalents.

Based on the foregoing, it can be appreciated that a number of embodiments including preferred and alternative embodiments, are disclosed herein. For example, in an embodiment, a gas sensor system can include a plurality of sensors, a microcontroller that receives sensor measurements from the plurality of sensors, and a pulse width modulation (PWM) demodulator, wherein feedback from the plurality of sensors generates a sensor offset and wherein the PWM demodulator is varied to reduce the sensor offset to null and provide sensor-to-sensor variations, which are independent of error in the sensor measurements.

In an embodiment, the plurality of sensors can comprise one or more temperature sensors.

In an embodiment, the plurality of sensors can comprise one or more pressure sensors.

In an embodiment, the plurality of sensors can comprise one or more humidity sensors.

In an embodiment, the plurality of sensors can comprise one or more temperature sensors, one or more pressure sensors and/or one or humidity sensors.

In an embodiment, a reference analog signal can be generated with a compensation algorithm and the reference analog signal can be used for zeroing the sensor offset.

In an embodiment, the compensation algorithm can use temperature and humidity sensor values from the sensor measurements to generate the sensor offset.

In an embodiment, an output can be varied in a closed loop to nullify the sensor offset.

In an embodiment, a method of operating a gas sensor system, can involve: receiving sensor measurements from a plurality of sensors; generating a sensor offset from feedback from the plurality of sensors; and varying a pulse width modulation (PWM) demodulator to reduce the sensor offset to null and provide sensor-to-sensor variations independent of error in the sensor measurements.

An embodiment of the method can further involve generating a reference analog signal with a compensation algorithm and using the reference analog signal for zeroing the sensor offset.

In an embodiment of the method, the compensation algorithm can use temperature and humidity sensor values from the sensor measurements to generate the sensor offset.

An embodiment of the method can further involve varying an output in a closed loop to nullify the sensor offset.

In another embodiment, a gas sensor system can include one or more processors and a memory, wherein the memory can store instruction to cause the one or more processors to perform: receiving sensor measurements from a plurality of sensors; generating a sensor offset from feedback from the plurality of sensors; and varying a pulse width modulation (PWM) demodulator to reduce the sensor offset to null and provide sensor-to-sensor variations independent of error in the sensor measurements.

In an embodiment, the instructions can cause the one or more processors to perform generating a reference analog signal with a compensation algorithm and using the reference analog signal for zeroing the sensor offset. In addition, a compensation algorithm can use temperature and humidity sensor values from the sensor measurements to generate the sensor offset.

In an embodiment, the instructions can cause the one or more processors to perform: varying an output in a closed loop to nullify the sensor offset.

It will be appreciated that variations of the above-disclosed and other features and functions, or alternatives thereof, may be desirably combined into many other different systems or applications. It will also be appreciated that various presently unforeseen or unanticipated alternatives, modifications, variations or improvements therein may be subsequently made by those skilled in the art which are also intended to be encompassed by the following claims.

What is claimed is:

1. A gas sensor system, comprising:
an electrochemical sensor configured to generate output data, wherein the output data is indicative of a concentration of a gay;
a plurality of sensors;
a microcontroller configured to receive sensor measurements from the plurality of sensors wherein the microcontroller is configured to generate a pulse width modulated (PWM) signal based on the sensor measurements; and
a pulse width modulation (PWM) demodulator configured to generate a compensation signal based on the PWM signal, wherein the compensation signal is utilized to reduce a sensor offset in the output data to null and provide sensor-to-sensor variations, which are independent of error in the sensor measurements.

2. The gas sensor system of claim 1 wherein the plurality of sensors comprises at least one temperature sensor.

3. The gas sensor system of claim 1 wherein the plurality of sensors comprises at least one pressure sensor.

4. The gas sensor system of claim 1 wherein the plurality of sensors comprises at least one humidity sensor.

5. The gas sensor system of claim 1, wherein the plurality of sensors comprises a humidity sensor and a temperature sensor wherein the PWM signal is generated based on temperature sensor value and humidity sensor value determined by the humidity sensor and the temperature sensor.

6. The gas sensor system of claim 1, wherein the PWM signal is varied in a closed loop to nullify the sensor offset.

7. A method of operating a gas sensor system, the method comprising:

receiving, by a microcontroller, an output data indicative of a concentration of a gas;
receiving, by the microcontroller, sensor measurements from a plurality of sensors;
generating by the microcontroller, a pulse width modulated (PWM) signal based on the sensor measurements; and
generating a compensation signal based on the PWM signal, wherein the compensation signal is utilized to reduce the sensor offset to null and provide sensor-to-sensor variations independent of error in the sensor measurements.

8. The method of claim 7 wherein the plurality of sensors comprises at least one temperature sensor.

9. The method of claim 7 wherein the plurality of sensors comprises at least one pressure sensor.

10. The method of claim 7 wherein the plurality of sensors comprises at least one humidity sensor.

11. The method of claim 7, wherein the plurality of sensors comprises a humidity sensor and a temperature sensor, wherein the PWM signal is generated based on temperature sensor value and a humidity sensor value.

12. The method of claim 7, wherein the PWM signal is varied in a closed loop to nullify the sensor offset.

13. A gas sensor system, comprising:
at least one processor and a memory storing instructions to cause the at least one processor to perform:
receiving an output data indicative of a concentration of a gas:
receiving sensor measurements from a plurality of sensors;
generating a pulse width modulated (PWM) signal based on the sensor measurements; and
generating a compensation signal based on the PWM signal, wherein the compensation signal is utilized to reduce the sensor offset to null and provide sensor-to-sensor variations independent of error in the sensor measurements.

14. The gas sensor system of claim 13, wherein the plurality of sensors comprises a humidity sensor and a temperature sensor, wherein the PWM signal is generated based on a temperature sensor value and a humidity sensor value.

15. The gas sensor system of claim 13 wherein the instructions cause the at least one processor to perform: varying the PWM signal in a closed loop to nullify the sensor offset.

* * * * *